US012779180B2

(12) United States Patent
Takahashi

(10) Patent No.: US 12,779,180 B2
(45) Date of Patent: Nov. 3, 2026

(54) GUIDE WIRE AND METHOD FOR PRODUCING GUIDE WIRE

(71) Applicant: ASAHI INTECC CO., LTD., Seto (JP)

(72) Inventor: Yasunao Takahashi, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 381 days.

(21) Appl. No.: 18/376,508

(22) Filed: Oct. 4, 2023

(65) Prior Publication Data

US 2024/0024639 A1 Jan. 25, 2024

Related U.S. Application Data

(63) Continuation of application No. PCT/JP2022/015803, filed on Mar. 30, 2022.

(30) Foreign Application Priority Data

Apr. 7, 2021 (JP) ................................ 2021-065056

(51) Int. Cl.
*A61M 25/09* (2006.01)

(52) U.S. Cl.
CPC ... *A61M 25/09* (2013.01); *A61M 2025/09083* (2013.01); *A61M 2025/09133* (2013.01)

(58) Field of Classification Search
CPC ........ A61M 25/09; A61M 2025/09058; A61M 2025/09083; A61M 2025/09091;
(Continued)

(56) References Cited

U.S. PATENT DOCUMENTS 5,171,383 A 12/1992 Sagae et al.
6,488,637 B1 * 12/2002 Eder ...................... A61L 31/10
600/585

(Continued)

FOREIGN PATENT DOCUMENTS

JP S63-171570 A 7/1988
JP H04-187159 A 7/1992

(Continued)

OTHER PUBLICATIONS

Chen, J et al. "On the factors affecting the critical indenter penetration for measurement of coating hardness". Vacuum vol. 83 p. 911-920. Elsevier. 2009.*

(Continued)

*Primary Examiner* — Adam J Eiseman
(74) *Attorney, Agent, or Firm* — Oliff PLC

(57) ABSTRACT

A guide wire that is durable against twisting stress includes a first shaft and a second shaft having a distal end joined to a proximal end of the first shaft. The second shaft is formed of a material exhibiting an elastic modulus higher than that of a material forming the first shaft. The second shaft includes a variable hardness portion including a first portion having a hardness that gradually decreases from a distal end to a proximal end of the first portion, and a second portion arranged proximally of the first portion, and exhibiting a hardness lower than the hardness of the distal end of the first portion. The length of the variable hardness portion in the axial direction of the guide wire is longer than the diameter of the second shaft.

9 Claims, 6 Drawing Sheets

(58) Field of Classification Search
CPC ......... A61M 2025/09133; A61M 2025/09141; A61M 2025/09175
USPC .......................................................... 600/585
See application file for complete search history.

(56) References Cited

U.S. PATENT DOCUMENTS

| | | | | |
|---|---|---|---|---|
| 8,052,620 | B2 * | 11/2011 | Ishida | A61M 25/09 600/585 |
| 8,337,519 | B2 * | 12/2012 | Wasicek | H04M 15/68 606/200 |
| 2004/0030266 | A1 | 2/2004 | Murayama et al. | |
| 2006/0150388 | A1 | 7/2006 | Inada et al. | |
| 2007/0149037 | A1 | 6/2007 | Souba et al. | |
| 2008/0234606 | A1 * | 9/2008 | Itou | A61M 25/09 600/585 |
| 2014/0200555 | A1 * | 7/2014 | Simpson | B23K 11/04 604/528 |
| 2016/0287842 | A1 * | 10/2016 | Sato | A61M 25/09 |
| 2021/0113818 | A1 * | 4/2021 | Yonezawa | A61M 25/09 |
| 2023/0302260 | A1 * | 9/2023 | Maruyama | A61M 25/09 |

FOREIGN PATENT DOCUMENTS

| | | | |
|---|---|---|---|
| JP | H11-514536 | A | 12/1999 |
| JP | 2004-230141 | A | 8/2004 |
| JP | 2004-243410 | A | 9/2004 |
| JP | 2007195952 | A | 8/2007 |
| JP | 6351628 | B2 | 7/2018 |
| WO | 97/16133 | A1 | 5/1997 |
| WO | 2014/113527 | A1 | 7/2014 |
| WO | 2020/219457 | A1 | 10/2020 |

OTHER PUBLICATIONS

Xu, et al. "Method for Determining Film Hardness and Thickness by Indentation." ASME Journal of Applied Mechanics, vol. 92. 2025.*

* cited by examiner

| Sample | Heat treatment | Number of twists |
|---|---|---|
| 1 | No | 10 |
| 2 | | 9 |
| 3 | | 10 |
| 4 | | 10 |
| 5 | Yes | 15 |
| 6 | | 19 |
| 7 | | 18 |
| 8 | | 14 |

FIG.4

GUIDE WIRE AND METHOD FOR PRODUCING GUIDE WIRE

CROSS-REFERENCE TO RELATED APPLICATIONS

This is a Continuation of Application No. PCT/JP2022/015803 filed Mar. 30, 2022, which claims priority to JP 2021-065056 filed Apr. 7, 2021. The disclosure of the prior applications is hereby incorporated by reference herein in its entirety.

TECHNICAL FIELD

The technology disclosed herein relates to a guide wire.

BACKGROUND

Methods using catheters are widespread as methods for treating or testing constricted parts or occluded parts (hereinafter referred to as "lesion(s)") of blood vessels etc. A guide wire is generally used for guiding a catheter to a lesion in a blood vessel etc. Some guide wires are known to include a first shaft and a second shaft having a distal end joined to the proximal end of the first shaft and being formed of a material exhibiting an elastic modulus higher than that of a material forming the first shaft (see, for example, Patent Literature 1). The first shaft arranged on the distal end side of the guide wire is formed of a material having a relatively low elastic modulus, thereby ensuring relatively high flexibility. On the other hand, the second shaft arranged on the proximal end side of the first shaft is formed of a material having a relatively high elastic modulus, thereby ensuring relatively high torquability from the proximal end side to the first shaft side of the guide wire.

CITATION LIST

Patent Literature

Patent Literature 1: WO 2014/113527

SUMMARY

Technical Problem

In the above guide wire including the first shaft and the second shaft, for example, when the guide wire is rotationally operated, the second shaft is subjected to strong twisting stress due to difference in hardness between the first shaft and the second shaft, which may result in reduced operability and resilience of the guide wire, for example. That is, regarding conventional guide wires, such a guide wire as a whole has low durability against twisting stress.

Technology capable of solving the above problems is disclosed herein.

Solution to Problem

The technology disclosed herein can be implemented as the following aspects, for example.

(1) The guide wire disclosed herein is a guide wire including a first shaft and a second shaft having a distal end joined to a proximal end of the first shaft and being formed of a material exhibiting an elastic modulus higher than that of a material forming the first shaft, wherein: the second shaft has a variable hardness portion having a first portion whose hardness gradually decreases from the distal end side of the second shaft toward the proximal end side of the second shaft, and a second portion being arranged closer to the proximal end side of the second shaft than the first portion, and exhibiting hardness lower than the hardness of the distal end of the first portion; and the length of the variable hardness portion in the axial direction of the guide wire is longer than the diameter of the second shaft.

In this guide wire, the second shaft has the variable hardness portion. The variable hardness portion has the first portion whose hardness gradually decreases from the distal end side of the second shaft toward the proximal end side of the second shaft, and the second portion being arranged closer to the proximal end side of the second shaft than the first portion, and exhibiting hardness lower than the hardness of the first portion. Therefore, according to this guide wire, the second shaft as a whole has improved durability against twisting stress compared to that of a configuration wherein the second shaft does not have any variable hardness portion. In addition, the length of the variable hardness portion in the axial direction of the guide wire is longer than the diameter of the second shaft. Therefore, according to this guide wire, the second shaft as a whole has more improved durability against twisting stress compared to that of a configuration wherein the length of the variable hardness portion in the axial direction of the guide wire is shorter than the diameter of the second shaft. Therefore, according to this guide wire, the durability of the guide wire as a whole against twisting stress can be improved.

(2) In the above guide wire, the second shaft may be configured in such a manner that the second shaft has a distal end portion including the distal end of the second shaft, and the variable hardness portion is arranged closer to the proximal end side of the second shaft than the distal end portion. According to this guide wire, compared to a configuration wherein the variable hardness portion is located at the distal end of the second shaft, a portion having relatively low hardness is present at a position that is away from the joint portion of the first shaft and the second shaft and is located on the proximal end side of the guide wire, and thus the durability of the guide wire as a whole against twisting stress can be more improved.

(3) In the above guide wire, the distal end portion of the second shaft may also be configured in such a manner that the distal end portion exhibits hardness lower than that of the distal end of the variable hardness portion. According to this guide wire, compared to a configuration wherein the hardness of the distal end portion of the second shaft is higher than the hardness of the distal end of the variable hardness portion, the durability of the guide wire as a whole against twisting stress can be more improved.

(4) In the above guide wire, the variable hardness portion may also be configured in such a manner that the variable hardness portion has a low hardness part exhibiting hardness lower than that of the distal end portion of the second shaft. According to this guide wire, compared to a configuration wherein the variable hardness portion does not have any low hardness part, the durability of the guide wire as a whole against twisting stress can be more improved.

(5) In the above guide wire, the low hardness part may also be configured in such a manner that the length of the low hardness part in the axial direction is longer than the diameter of the second shaft. According to this guide wire, compared to a configuration wherein the length of the low hardness part is shorter than the diameter of the second shaft, the durability of the guide wire as a whole against twisting stress can be more improved.

(6) In the above guide wire, the variable hardness portion may also be configured in such a manner that the variable hardness portion includes the distal end of the second shaft. According to this guide wire, compared to a configuration wherein the variable hardness portion does not include any distal end of the second shaft, production of unnecessary stress due to difference in hardness in the vicinity of the joint portion of the first shaft and the second shaft can be suppressed.

(7) In the above guide wire, the second shaft may also be configured in such a manner that the second shaft has a hardness increasing part being arranged closer to the proximal end side of the second shaft than the variable hardness portion and having hardness that gradually increases from the distal end side of the second shaft toward the proximal end side of the second shaft. According to this guide wire, for example, compared to a configuration wherein hardness increases in stages in a part located closer to the proximal end side than the variable hardness portion in the second shaft, the guide wire can be rotationally operated smoothly while improving the durability against twisting stress.

(8) The method for producing a guide wire disclosed herein is a method for producing a guide wire, comprising a step of preparing a first shaft member and a second shaft member formed of a material exhibiting an elastic modulus higher than that of a material forming the first shaft member, a step of joining the proximal end of the first shaft member and the distal end of the second shaft member, and a step of subjecting a portion of the second shaft member, which is located closer to the proximal end side of the second shaft member than the joint part of the first shaft member and the second shaft member, to heat treatment to soften the portion. Therefore, according to the method for producing a guide wire, a guide wire having the improved durability of the guide wire as a whole against twisting stress can be provided.

Note that in the production method of (8) above, the guide wire may be the guide wire described in any one of (1) to (7) above.

Note that the technology disclosed herein can be achieved in various aspects, such as guide wires and methods for producing the same.

BRIEF DESCRIPTION OF DRAWINGS

FIG. 4 is a diagram that shows performance evaluation results evaluated by a twisting test.

DETAILED DESCRIPTION

A. First Embodiment

A-1. Configuration of Guide Wire 100

Figure 1:
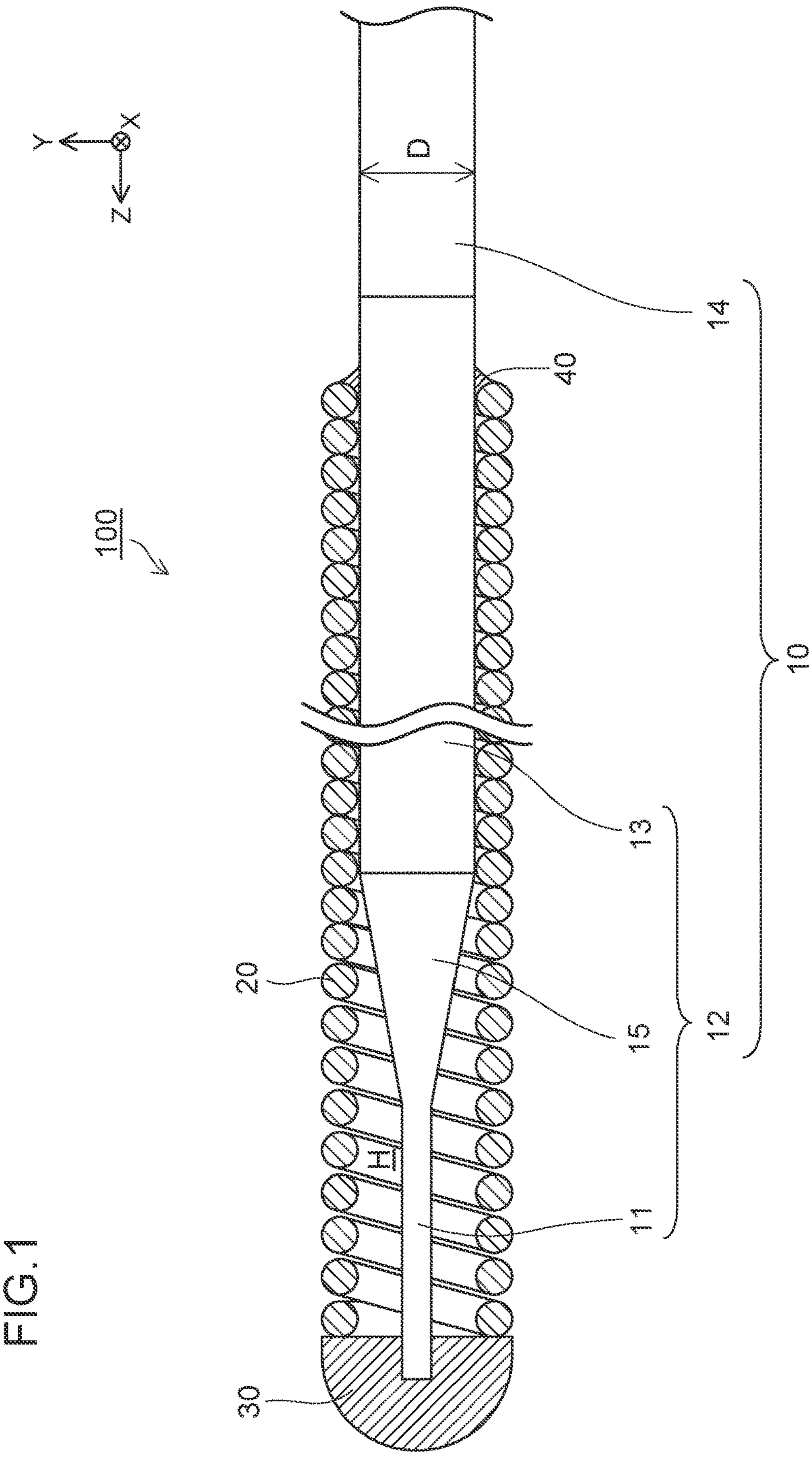
FIG. 1 is a diagram that schematically shows the configuration of a guide wire in a first embodiment.

FIG. 1 is a diagram that schematically shows the configuration of the guide wire 100 in the first embodiment. FIG. 1 shows the side (YZ side) configuration of the core shaft 10 and the vertical cross section (YZ cross section) of a coil body 20 and a distal tip 30 of the guide wire 100. In FIG. 1, Z axis positive direction side is the distal end side (distal side) to be inserted to a body, and Z axis negative direction side is the proximal end side (proximal side, near side) to be operated by a professional such as a doctor. FIG. 1 shows a state where the guide wire 100 is a straight line approximately parallel to the Z axis direction, as a whole, but the guide wire 100 is flexible enough to be bent. In the following description, regarding the guide wire 100 and each constituent member of the guide wire 100, a distal end and the vicinity thereof are referred to as a "distal end portion" and a proximal end and the vicinity thereof are referred to as a "proximal end portion".

The guide wire 100 is a medical device that is inserted into a blood vessel etc., in order to guide a catheter (not shown) to a lesion (constricted part or occluded part) in the blood vessel etc., for example. The axial length of the guide wire 100 is, for example, about 150 cm or more and 300 cm or less.

As shown in FIG. 1, the guide wire 100 includes the core shaft 10, the coil body 20, the distal tip 30, and a proximal end side joint part 40.

The core shaft 10 is a long member with a small diameter on the distal end side and a large diameter on the proximal end side. In this embodiment, the core shaft 10 has a distal end shaft 12 and a proximal end shaft 14. The distal end shaft 12 is an example of the first shaft in claims and the proximal end shaft 14 is an example of the second shaft in claims.

The distal end shaft 12 has a small diameter portion 11, a large diameter portion 13, and a tapered portion 15. In FIG. 1, a part of the large diameter portion 13 is omitted. The small diameter portion 11 is a portion including the distal end of the core shaft 10. The small diameter portion 11 has a rod shape with a circular cross section. The cross section is a section (XY section in this embodiment) orthogonal to the axial direction (Z-axis direction in this embodiment) of the core shaft 10. Note that in this embodiment, the axial direction of the core shaft 10 coincides with the axial direction of the guide wire 100. The large diameter portion 13 is located closer to the proximal end side of the core shaft 10 with respect to the small diameter portion 11, and has a rod shape such that the cross section is a circle with an outer diameter larger than that of the small diameter portion 11. The tapered portion 15 is located between the small diameter portion 11 and the large diameter portion 13. The tapered portion 15 has an outer diameter gradually increasing from the boundary position with the small diameter portion 11 toward the boundary position with the large diameter portion 13. The outer diameter of the small diameter portion 11 is about 0.03 mm or more and 0.085 mm or less, for example, and the outer diameter of the large diameter portion 13 is about 0.2 or more and 0.9 mm or less, for example. The shape of the cross section of each part of the core shaft 10 is not particularly limited, and may be polygonal such as triangular or quadrangular, for example.

The proximal end shaft 14 is located at the end of the proximal end of the core shaft 10 with respect to the distal end shaft 12, and the proximal end of the distal end shaft 12 and the distal end of the proximal end shaft 14 are joined by welding. The proximal end shaft 14 has a rod shape with a circular cross section wherein the outer diameter is substantially the same as that of the large diameter portion 13 of the distal end shaft 12. Note that the axial length of the distal end shaft 12 is about 10 cm or more and 50 cm or less, and the axial length of the proximal end shaft 14 is about 100 cm or more and 200 cm or less.

As a material for forming the core shaft 10, known materials are used, and metal materials, more specifically, stainless steel (SUS302, SUS304, SUS316 etc.), superelastic alloys such as Ni—Ti alloys, piano wires, nickel-chromium alloys, cobalt alloys, tungsten, etc. are used, for example. However, the elastic modulus of the material forming the proximal end shaft 14 is higher than the elastic modulus of the material forming the distal end shaft 12. In this embodiment, for example, the material forming the distal end shaft 12 is an Ni—Ti alloy and the material forming the proximal end shaft 14 is stainless steel.

As shown in FIG. 1, the coil body 20 is a hollow-cylindrically-shaped coiled member formed by winding one wire spirally. In this embodiment, the coil body 20 is arranged so as to surround the outer periphery of the distal end portion of the core shaft 10 (specifically, the small diameter portion 11, the tapered portion 15, and a part of the large diameter portion 13). An inner cavity H is formed between the core shaft 10 and the coil body 20. The full length of the coil body 20 is about 10 mm or more and 500 mm or less, for example, and the outer diameter of the coil body 20 is about 0.2 mm or more and 0.9 mm or less, for example.

As materials for forming and configuring the coil body 20, known materials are used, and metal materials, more specifically, platinum, stainless steel (e.g., SUS302, SUS304, and SUS316), superelastic alloys such as Ni—Ti alloys, piano wires, nickel-chromium alloys, cobalt alloys, tungsten, etc. are used, for example.

The distal tip 30 is a member that joins the distal end portion of the core shaft 10 and the distal end portion of the coil body 20. The distal end of the core shaft 10 and the distal end of the coil body 20 are fixed in such a manner that they are embedded inside the distal tip 30. The outer peripheral surface on the distal end side of the distal tip 30 is a smooth surface (for example, approximate semi-spherical surface and cylindrical surface). As materials for configuring the distal tip 30, known materials are used and brazing materials (e.g., aluminum alloy solder, silver solder, and gold solder), metal solder (e.g., Ag—Sn alloy and Au—Sn alloy), and adhesives (e.g., epoxy-based adhesive) are used, for example. In this embodiment, an Ag—Sn alloy is used as the material for configuring the distal tip 30.

The proximal end side joint part 40 is a member that joins the proximal end side (large diameter portion 13) of the distal end shaft 12 of the core shaft 10 and the proximal end side of the coil body 20. As materials for configuring the proximal end side joint part 40, known materials are used and brazing materials (e.g., aluminum alloy solder, silver solder, and gold solder), metal solder (e.g., Ag—Sn alloy and Au—Sn alloy), and adhesives (e.g., epoxy-based adhesive) are used, for example. In this embodiment, an Ag—Sn alloy is used as the material for configuring the proximal end side joint part 40.

A-2. Detailed Configuration in the Vicinity of the Joint Part of the Core Shaft 10

Figure 2:
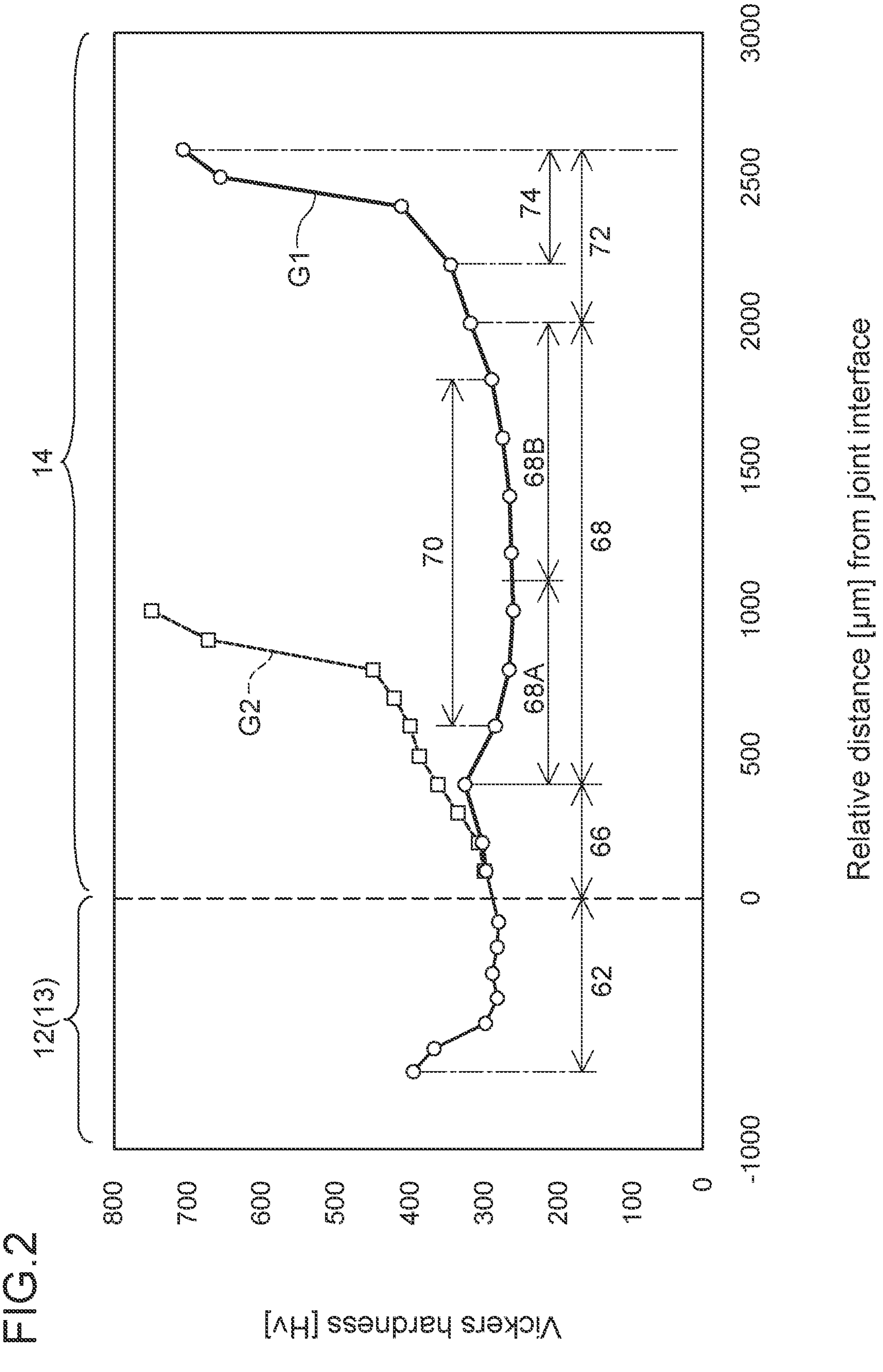
FIG. 2 is a diagram that shows Vickers hardness in the vicinity of the joint part of a core shaft.

FIG. 2 is a diagram that shows Vickers hardness in the vicinity of the joint part of the core shaft 10. In FIG. 2, the vertical axis indicates the Vickers hardness (Hv), and the horizontal axis indicates the relative distance from the joint interface in the axial direction of the core shaft 10. “0” on the horizontal axis means the position of the joint interface of the core shaft 10 (the joint site of the distal end shaft 12 and the proximal end shaft 14). In FIG. 2, the Vickers hardness of the distal end shaft 12 is shown on the left with respect to the joint interface, and the Vickers hardness of the proximal end shaft 14 is shown on the right with respect to the joint interface. In FIG. 2, graph G1 indicates the Vickers hardness of the guide wire 100 of this embodiment, and graph G2 indicates the Vickers hardnesses of guide wires (not shown) of the comparative examples. Comparative examples are samples 1 to 4, and G31 to G33 described later.

A method for measuring the Vickers hardness at each site of the core shaft 10 is as follows. Vickers hardness is measured by a method according to JIS2244. In this embodiment, the Vickers hardness of the central portion (in the vicinity of the central axis) of each site of the core shaft 10 is measured and used as the hardness of each site. Specifically, a test piece in the vicinity of the joint part of the core shaft 10 is cut along the axial direction to obtain a longitudinal section (YZ section) including the central portion. Subsequently, a quadrangular pyramid-shaped indenter is pressed against the longitudinal section of the test piece with a constant load (test force: F (N), 0.1 N/sec), and then the average length d (mm) of the diagonal line of an indentation (dent) formed when the indenter is removed is measured. The Vickers hardness is determined by substituting the test force F and the average diagonal length d into the following formula for calculation. The load (test force) used in this test is 1N. The load (test force) is preferably 1 N, and Vickers hardness measured with a load of 1 N or less is sometimes called micro Vickers hardness.

$$\text{Vickers hardness}=0.01891\times F/d^2$$

As shown in FIG. 2, the proximal end shaft 14 has a variable hardness portion 68. The variable hardness portion 68 has a first portion 68A and a second portion 68B. The first portion 68A is a portion whose hardness gradually decreases from the distal end side of the proximal end shaft 14 toward the proximal end side of the proximal end shaft 14. The second portion 68B is a portion being arranged closer to the proximal end side of the proximal end shaft 14 than the first portion 68A, and exhibiting hardness lower than the hardness of the distal end of the first portion 68A. In this embodiment, the first portion 68A and the second portion 68B are axially adjacent to each other. Further, as shown in FIG. 2, in the variable hardness portion 68, the hardness continuously decreases from the distal end of the variable hardness portion 68 toward the central portion of the variable hardness portion 68, and continuously increases from the central portion toward the proximal end of the variable hardness portion 68. The length of the variable hardness portion 68 in the axial direction of the guide wire 100 is longer than the diameter D (see FIG. 1) of the proximal end shaft 14. In this embodiment, the length of the variable hardness portion 68 is, for example, about 1,500 μm or more and 1,700 μm.

The proximal end shaft 14 further has a distal end portion 66. The distal end portion 66 includes the distal end of the proximal end shaft 14 (the distal end surface facing the joint interface). Specifically, the variable hardness portion 68 is arranged closer to the proximal end side of the proximal end shaft 14 than the distal end portion 66. In this embodiment, the distal end portion 66 and the variable hardness portion 68 are axially adjacent to each other. The hardness of the distal end portion 66 is lower than the hardness of the distal end of the variable hardness portion 68.

The variable hardness portion 68 has a low hardness part 70. The low hardness part 70 is a portion of the variable hardness portion 68, which exhibits hardness lower than the hardness of the distal end portion 66 of the proximal end shaft 14. In this embodiment, as shown in FIG. 2, in the low hardness part 70, the hardness continuously decreases from the distal end of the low hardness part 70 toward the central portion of the low hardness part 70, and continuously increases from the central portion toward the proximal end of the low hardness part 70. The length of the low hardness part 70 in the axial direction (Z axis direction) is longer than the diameter D of the proximal end shaft 14.

The proximal end shaft 14 has a hardness increasing part 72. The hardness increasing part 72 is arranged closer to the proximal end side of the proximal end shaft 14 than the variable hardness portion 68. The hardness increasing part 72 is a portion whose hardness gradually increases from the distal end side of the proximal end shaft 14 toward the proximal end side of the proximal end shaft 14. The hardness increasing part 72 has a steep part 74. The inclination angle of the steep part 74 with respect to the axial direction of the guide wire 100 is greater than the inclination angle of the variable hardness portion 68 with respect to the axial direction of the guide wire 100. Specifically, the hardness of the proximal end shaft 14 increases abruptly in the steep part 74.

The distal end shaft 12 has a proximal end portion 62 including the proximal end of the distal end shaft 12. The hardness of the proximal end portion 62 is lower than the hardness of a portion of the distal end shaft 12, which is located closer to the distal end side than the proximal end portion 62. The proximal end portion 62 of the distal end shaft 12 and the distal end portion 66 of the proximal end shaft 14 are a welded part formed in a joining step (S120) of the production method described later.

A-3. Method for Producing Guide Wire 100

Figure 3:
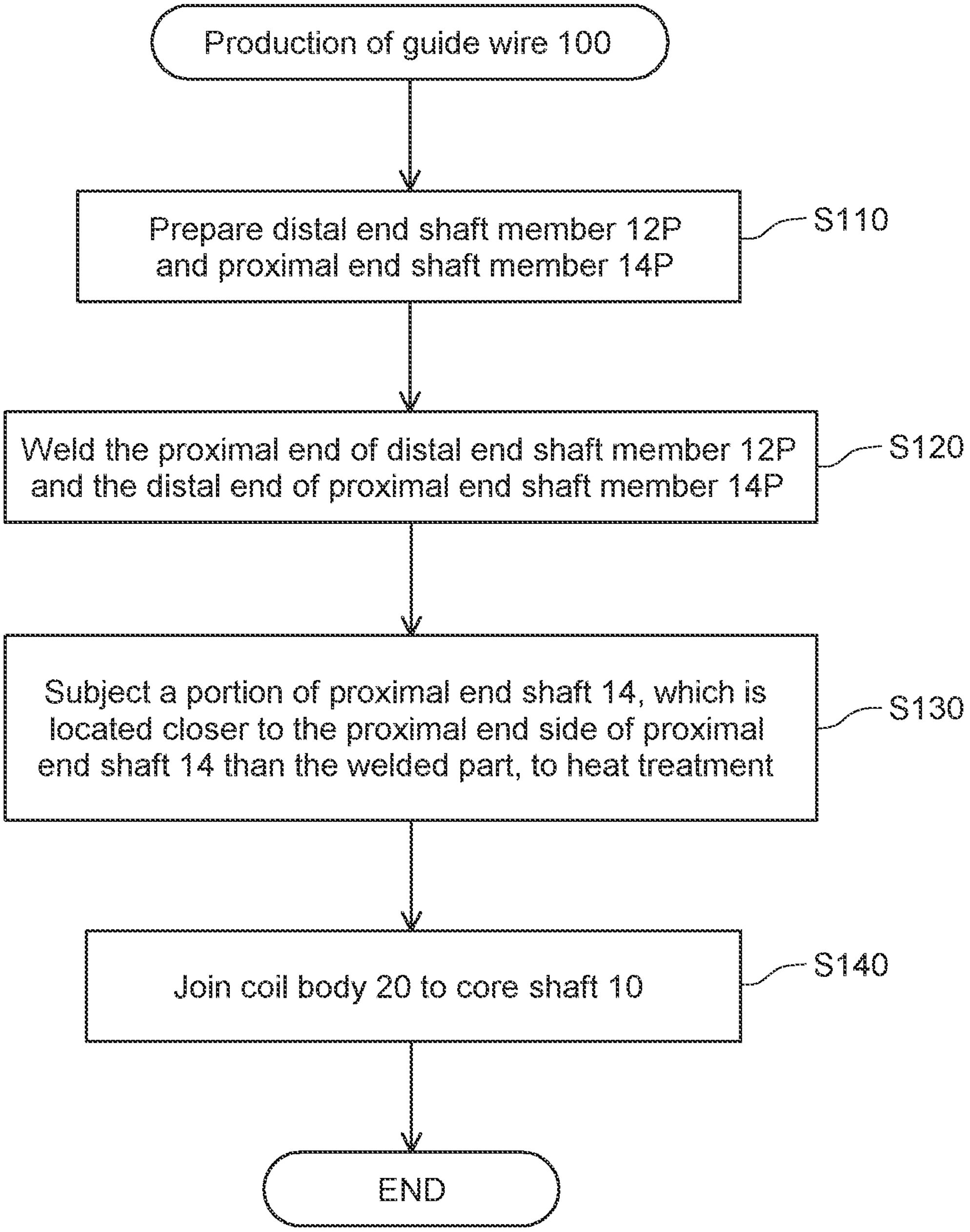
FIG. 3 is a flow chart that shows the production process of the guide wire.

FIG. 3 is a flow chart that shows the production process of the guide wire 100. The guide wire 100 of this embodiment can be produced by the following method, for example.

As shown in FIG. 3, first, a distal end shaft member 12P and a proximal end shaft member 14P, the shapes of which are processed by mechanical polishing or the like, are prepared (S110). The distal end shaft member 12P corresponds to the distal end shaft 12 before being joined (welded) to the proximal end shaft member 14P. The proximal end shaft member 14P corresponds to the proximal end shaft 14 before being joined (welded) to the distal end shaft member 12P. The elastic modulus of the material (for example, stainless steel) forming the proximal end shaft member 14P is higher than the elastic modulus of the material (for example, Ni—Ti alloy) forming the distal end shaft member 12P. In addition, the distal end shaft member 12P is an example of the first shaft member in claims and the proximal end shaft member 14P is an example of the second shaft member in claims.

Next, the proximal end of the distal end shaft member 12P and the distal end of the proximal end shaft member 14P are welded (S120). As a result of this welding, a welded part (the proximal end portion 62 of the distal end shaft 12 and the distal end portion 66 of the proximal end shaft 14) is formed at the joint portion of the distal end shaft member 12P and the proximal end shaft member 14P.

Next, a portion of the proximal end shaft 14, which is located closer to the proximal end side of the proximal end shaft 14 than the welded part, is subjected to a heat treatment procedure for softening (S130). As the heat treatment, a known method can be used, and an example thereof may be an electrification method that involves passing an electric current between both ends of an area(s) to be subjected to heat treatment to generate heat, or a method that involves irradiating an area(s) to be subjected to heat treatment with laser light for heating. As a result, in addition to the welded part, the core shaft 10 having the variable hardness portion 68 etc., is produced. Note that, as a result of this heat treatment, in the guide wire 100, the heat-affected range (the distal end portion 66, the variable hardness portion 68, the hardness increasing part 72) due to welding in the proximal end shaft 14 of the core shaft 10 is longer than the heat-affected range (proximal end portion 62) in the distal end shaft 12. For example, when the proximal end shaft 14 is made of stainless steel, the portion corresponding to the variable hardness portion 68 of the proximal end shaft 14 is heated to a temperature range of, for example, 300° C. or higher and 800° C. or lower.

Next, the coil body 20 is joined to the core shaft 10 (S140). Specifically, the coil body 20 produced by winding a coil wire is prepared, the core shaft 10 is inserted into the hollow part of the coil body 20 to form a distal tip 30 and the proximal end side joint part 40 for joining the coil body 20 and the core shaft 10. In addition, the distal tip 30 is formed by, for example, injecting a molten resin into a mold capable of forming the shape of the distal tip 30, and then immersing the core shaft 10 and the distal end portion of the coil body 20 therein, followed by cooling. The proximal end side joint part 40 is formed by brazing it to the core shaft 10 on the proximal end side of the coil body 20. For example, the guide wire 100 having the above configuration can be produced by the above-described method.

A-4. Effect of this Embodiment

As described above, the guide wire 100 of this embodiment includes the core shaft 10 having the distal end shaft 12 and the proximal end shaft 14 (see FIG. 1). The proximal end shaft 14 has the distal end joined to the proximal end of the distal end shaft 12. The proximal end shaft 14 is formed of a material exhibiting an elastic modulus higher than that of the material forming the distal end shaft 12. The proximal end shaft 14 has a variable hardness portion 68 (see FIG. 2). The variable hardness portion 68 has a first portion 68A and a second portion 68B. The first portion 68A is a portion whose hardness gradually decreases from the distal end side of the proximal end shaft 14 toward the proximal end side of the proximal end shaft 14. The second portion 68B is a portion being arranged closer to the proximal end side of the proximal end shaft 14 than the first portion 68A, and exhibiting hardness lower than the hardness of the distal end of the first portion 68A.

Therefore, in this embodiment, compared to a configuration wherein the proximal end shaft 14 does not have the variable hardness portion 68, the durability of the proximal end shaft 14 as a whole against twisting stress is more improved. In addition, the length of the variable hardness portion 68 in the axial direction of the guide wire 100 is longer than the diameter of the proximal end shaft 14. Therefore, in this embodiment, compared to a configuration wherein the length of the variable hardness portion 68 is shorter than the diameter of the proximal end shaft 14, the durability of the proximal end shaft 14 as a whole against twisting stress is more improved. Therefore, according to this embodiment, improvement in the durability against twisting stress of the proximal end shaft 14 having a relatively high elastic modulus can improve the durability of the guide wire 100 as a whole against twisting stress. Note that the length of the variable hardness portion 68 in the axial direction of the guide wire 100 is one hundredth or less of the length of the proximal end shaft 14, and thus the torquability of the proximal end shaft 14 is not significantly decreased due to the presence of the variable hardness portion 68.

In this embodiment, the proximal end shaft 14 further has the distal end portion 66 (see FIG. 2). The distal end portion 66 includes the distal end of the proximal end shaft 14. Accordingly, in this embodiment, compared to a configuration wherein the variable hardness portion 68 is located at the distal end of the proximal end shaft 14, a portion having relatively low hardness is present at a position on the proximal end side of the guide wire 100, which is away from the joint portion of the distal end shaft 12 and the proximal end shaft 14. Therefore, according to this embodiment, the durability of the guide wire 100 as a whole against twisting stress can be more improved. Further, in this embodiment, the variable hardness portion 68 is located closer to the proximal end side of the guide wire 100 than the welded part (the proximal end portion 62 of the distal end shaft 12, the distal end portion 66 of the proximal end shaft 14) having originally low hardness. Therefore, while a decrease in the joint strength of the welded part for joining the distal end shaft 12 and the proximal end shaft 14 is suppressed, the durability of the guide wire 100 as a whole against twisting stress is improved.

In this embodiment, the hardness of the distal end portion 66 is lower than the hardness of the distal end of the variable hardness portion 68. Hence, according to this embodiment, compared to a configuration wherein the hardness of the distal end portion 66 of the proximal end shaft 14 is higher than the hardness of the distal end of the variable hardness portion 68, the durability of the guide wire 100 as a whole against twisting stress can be more improved. Further, a portion with relatively high hardness is present at the boundary between the distal end portion 66 and the variable hardness portion 68. Accordingly, for example, compared to a configuration wherein such a portion with relatively high hardness is absent at the boundary between the distal end portion 66 and the variable hardness portion 68, the shorter the part where a portion(s) with low hardness is present continuously in the axial direction, the more suppressed decrease in torquability of the proximal end shaft 14 due to the presence of the variable hardness portion 68.

In this embodiment, the variable hardness portion 68 has the low hardness part 70. The low hardness part 70 is a portion of the variable hardness portion 68, which exhibits hardness lower than the hardness of the distal end portion 66 of the proximal end shaft 14. Therefore, according to this embodiment, compared to a configuration wherein the variable hardness portion 68 does not have the low hardness part 70, the durability of the guide wire 100 as a whole against twisting stress can be more improved.

In this embodiment, the length of the low hardness part 70 in the axial direction (Z axis direction) is longer than the diameter D of the proximal end shaft 14. Therefore, according to this embodiment, compared to a configuration wherein the length of the low hardness part 70 is shorter than the diameter of the proximal end shaft 14, the durability of the guide wire 100 as a whole against twisting stress can be more improved.

In this embodiment, the proximal end shaft 14 has a hardness increasing part 72. The hardness increasing part 72 is arranged closer to the proximal end side of the proximal end shaft 14 than the variable hardness portion 68. The hardness increasing part 72 is a portion whose hardness gradually increases from the distal end side of the proximal end shaft 14 toward the proximal end side of the proximal end shaft 14. Therefore, according to this embodiment, for example, compared to a configuration wherein the hardness increases in stages in a portion located closer to the proximal end side than the variable hardness portion 68 in the proximal end shaft 14, the guide wire 100 can be rotationally operated smoothly while improving the durability against twisting stress.

A-5. Performance Evaluation

Performance evaluation made using a plurality of core shaft 10 samples is as described below. FIG. 4 is a diagram that shows performance evaluation results evaluated by a twisting test. Samples 1 to 8 were prepared by joining the above distal end shaft member 12P (made of Ni—Ti alloy) and proximal end shaft member 14P (made of stainless steel) by welding (see S120 in FIG. 3) under the same conditions mutually. However, samples 1 to 4 were not subjected to heat treatment (S130 in FIG. 3) for forming the variable hardness portion 68, and samples 5 to 8 were subjected to the heat treatment under the same conditions mutually. Through the heat treatment, a portion corresponding to the variable hardness portion 68 of the proximal end shaft member 14 was heated to a temperature of about 500° C. The axial length of each of samples 1 to 8 is about 100 mm, and the joint interface is located at the center in the axial direction of each sample. Further, the diameter of each of samples 1 to 8 is about 0.3 mm.

A twisting test was performed by applying a twisting force to each of samples 1 to 8. In the twisting test, one end of each of samples 1 to 8 was fixed and the other end was rotated to apply a twisting force. "Number of twists" in FIG. 4 is the number of twists applied when each of samples 1 to 8 was broken. The rotational direction for samples 1, 3, 5 and 7 was opposite to the same for samples 2, 4, 6 and 8.

As shown in FIG. 4, according to the results of the twisting test, it can be seen that the number of twists applied to each of samples 5 to 8 is generally greater than that applied to each of samples 1 to 4. This means that as a result of the formation of the variable hardness portion 68 by subjecting the proximal end shaft 14 to heat treatment, the durability of the guide wire 100 as a whole against twisting stress was improved.

Figure 5:
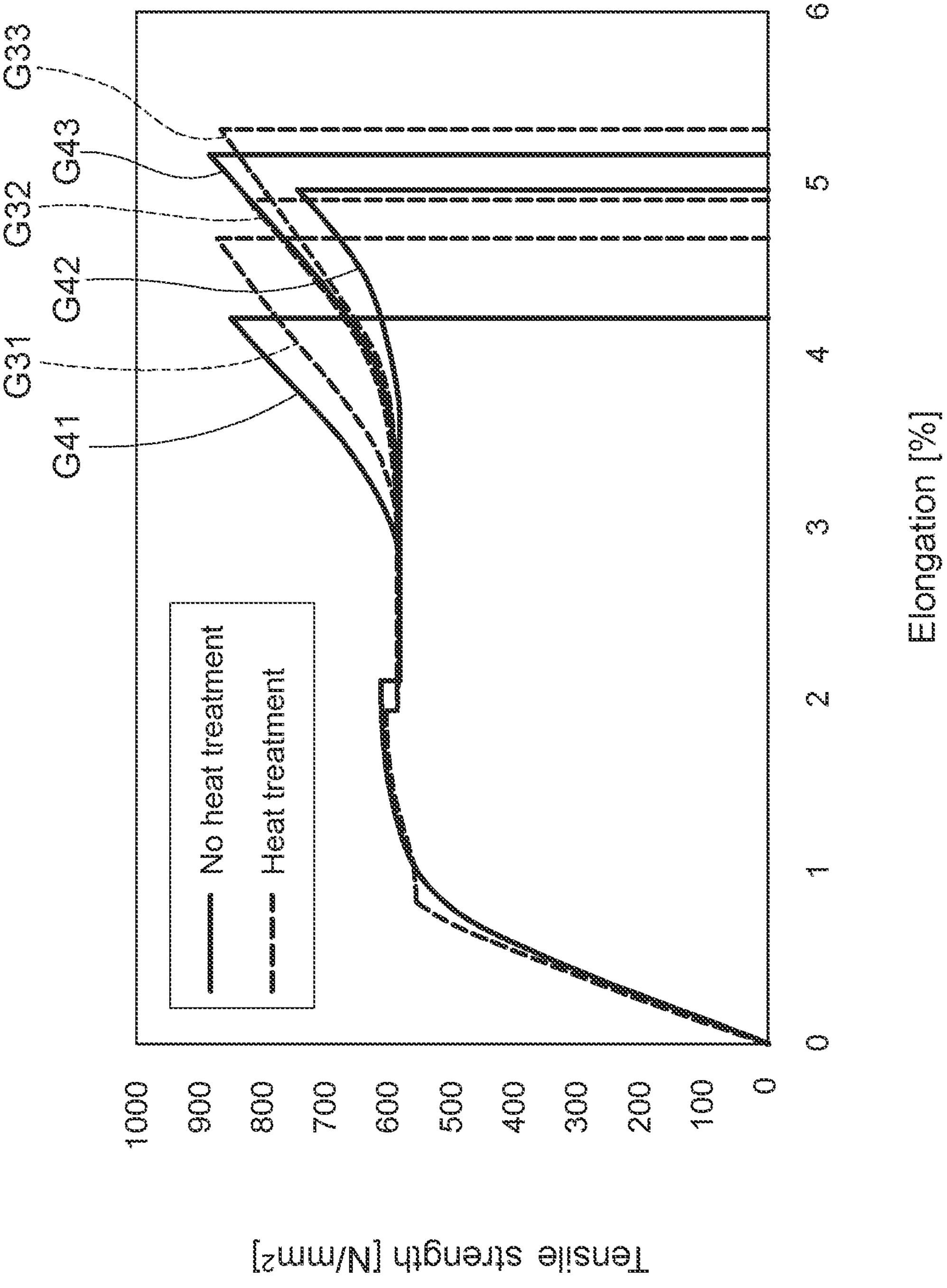
FIG. 5 is a diagram that shows performance evaluation results evaluated by a tensile test.

FIG. 5 is a diagram that shows performance evaluation results evaluated by a tensile test. Samples G31 to G43 were prepared by joining the above distal end shaft member 12P (made of Ni—Ti alloy) and proximal end shaft member 14P (made of stainless steel) by welding (see S120 in FIG. 3) under the same conditions mutually. However, samples G31 to G33 were not subjected to heat treatment (S130 in FIG. 3) for forming the variable hardness portion 68, and samples G41 to G43 were subjected to the heat treatment under the same conditions mutually. Through the heat treatment, a portion corresponding to the variable hardness portion 68 of the proximal end shaft member 14 was heated to a temperature of about 500° C. The axial length of each of samples G31 to G43 is about 100 mm, and the joint interface is located at the center in the axial direction of each sample. Further, the diameter of each of samples G31 to G43 is about 0.3 mm.

A tensile test was performed on each of samples G31 to G43. Under the tensile test conditions of a standard state (temperature 20° C., relative humidity 65%), the tensile speed of 200 mm/min, and the distance between grippers of 100 mm, load (tensile strength (N/mm$^2$)) applied when a sample was broken, and elongation (%) were measured.

As shown in FIG. 5, according to the results of the tensile test, all of samples G31 to G43 had approximately the same tensile strength and elongation. In both samples G31 to G43 and samples G31 to G43, the range of variation in tensile strength was within a predetermined range (700 N/mm$^2$ or more and 900 N/mm$^2$ or less), and the range of variation in elongation was within a predetermined range (4% or more and 5.5% or less). This means that even if the proximal end shaft 14 is subjected to heat treatment to form the variable hardness portion 68, a decrease in the strength of the guide wire 100 is not affected.

B. Second Embodiment

Figure 6:
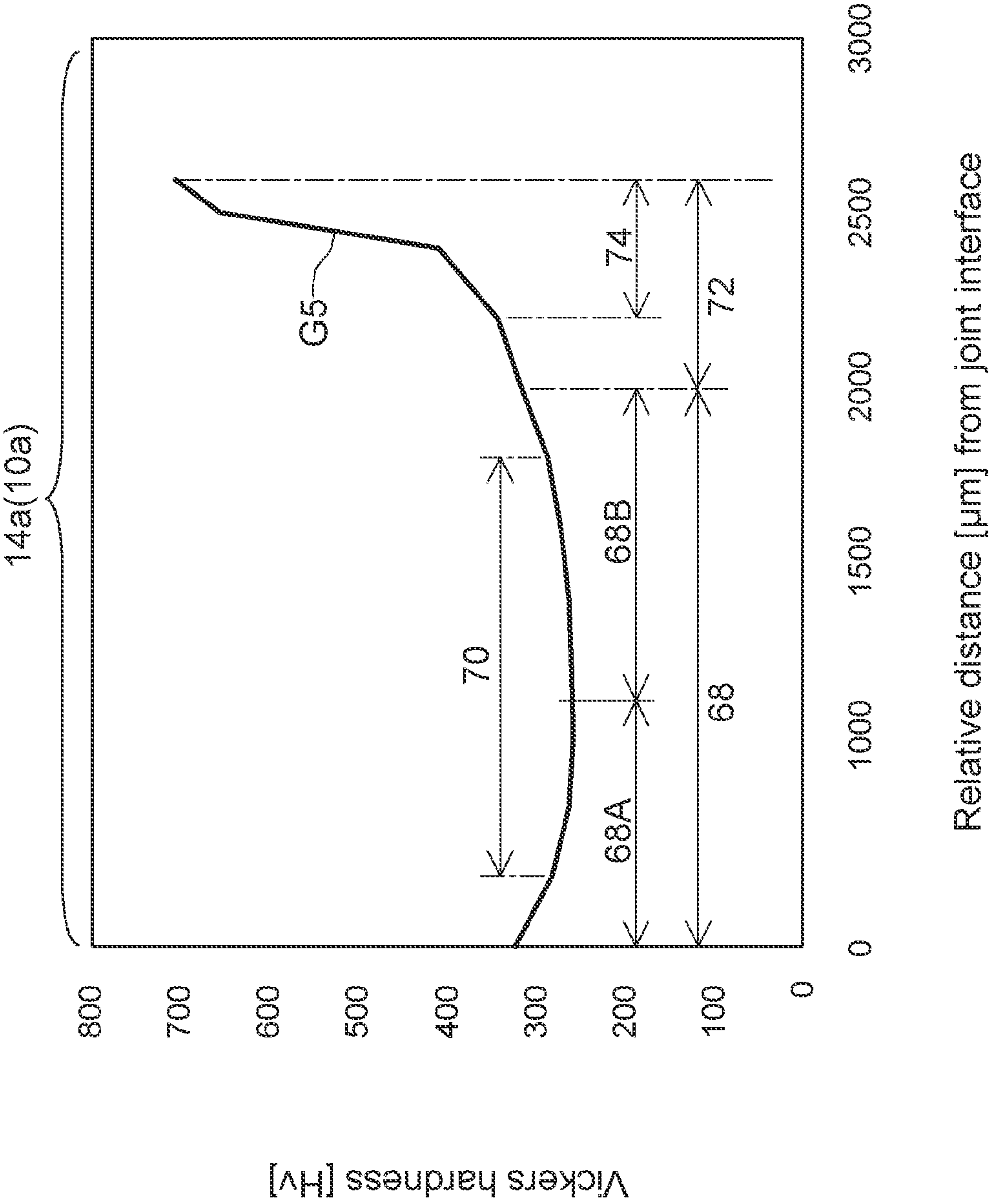
FIG. 6 is a diagram that shows Vickers hardness in the vicinity of the joint part of the core shaft in the second embodiment.

FIG. 6 is a diagram that shows Vickers hardness in the vicinity of the joint part of a core shaft 10*a* in the second embodiment. Hereinafter, the description of any component of the core shaft 10*a* in the second embodiment, which is the same as that of the core shaft 10 of the first embodiment, is omitted as appropriate by marking it with the same symbol.

The core shaft 10*a* of the second embodiment differs from the core shaft 10 of the first embodiment in terms of the configuration of the proximal end shaft 14*a*. Specifically, in the proximal end shaft 14 of the first embodiment, the distal end portion 66 was formed closer to the distal end side of the proximal end shaft 14 than the variable hardness portion 68. In contrast, in the proximal end shaft 14*a* of the second embodiment, the variable hardness portion 68 includes the distal end of the proximal end shaft 14. Therefore, according to the second embodiment, compared to a configuration wherein the variable hardness portion 68 does not include the distal end of the proximal end shaft 14*a*, production of unnecessary stress due to difference in hardness in the vicinity of the joint portion of the distal end shaft 12 and the proximal end shaft 14*a* can be suppressed.

C. Modification Example

The technology disclosed herein is not limited to the above embodiments, and can be modified in various forms without departing from the gist thereof. For example, the following modification examples are also possible.

The configurations of the guide wire 100 and the core shaft 10, 10*a* in the above embodiments are only examples and can be modified variously. For example, the shape of distal end shaft 12 may be cylindrical with the same outer diameter over its entire length. Moreover, the distal end shaft 12 and the proximal end shaft 14, 14*a* may be joined not only by welding but also by other joining methods (for example, adhesion, etc.).

In each of the above embodiments, the Vickers hardness at the central portion (in the vicinity of the center axis) of each site of the core shaft 10, 10*a* was measured to determine the hardness of each site. However, the way for the measurement is not limited thereto, and Vickers hardness of the outer peripheral surface of each site of the core shaft 10, 10*a* may be measured and used as the hardness of each site, for example.

In the above first embodiment, in the core shaft 10, the hardness of the distal end portion 66 may be the same as the hardness of the distal end of the variable hardness portion 68 or may be higher than the hardness of the distal end of the variable hardness portion 68. In each of the above embodiments, in the core shaft 10, 10*a*, the variable hardness portion 68 does not have to have the low hardness part 70.

In each of the above embodiments, the length of the low hardness part 70 in the axial direction may be the same as the diameter D of the proximal end shaft 14 or may be shorter than the diameter D of the proximal end shaft 14. In each of the above embodiments, the proximal end shaft 14 does not have to have the hardness increasing part 72.

The materials for each member in each of the above embodiments are only examples, and can be modified variously. The methods for producing the guide wire in the above embodiments are only examples and can be modified variously.

REFERENCE SIGNS LIST

10, 10*a*: core shaft, 11: small diameter portion, 12: distal end shaft, 12P: distal end shaft member, 13: large diameter portion, 14, 14*a*: proximal end shaft, 14P: proximal end shaft member, 15: tapered portion, 20: coil body, 30: distal tip, 40: proximal end side joint part, 62: proximal end portion, 66: distal end portion, 68: variable hardness portion, 68A: first portion, 68B: second portion, 70: low hardness part, 72: hardness increasing part, 74: steep part, 100: guide wire, H: inner cavity

The invention claimed is:

1. A guide wire, comprising:
- a first shaft, and
- a second shaft including a distal end joined to a proximal end of the first shaft, the second shaft being formed of a material exhibiting an elastic modulus higher than an elastic modulus of a material forming the first shaft, wherein:
- the second shaft includes a variable hardness portion formed by heat treatment comprising:
  - a first portion having a hardness that gradually decreases from a distal end of the first portion to a proximal end of the first portion, and
  - a second portion arranged proximally of the first portion, the second portion exhibiting a hardness lower than the hardness of the distal end of the first portion,
- a length of the variable hardness portion in an axial direction of the guide wire is longer than a diameter of the second shaft, and
- the hardness of each of the first portion and the second portion is a Vickers hardness measured at a central portion of a measurement site in a longitudinal section of the second shaft.

2. The guide wire according to claim 1, wherein the second shaft includes a distal end portion including the distal end of the second shaft, and the variable hardness portion is arranged proximally of the distal end portion.

3. The guide wire according to claim 2, wherein the distal end portion of the second shaft exhibits a hardness lower than a hardness of the distal end of the variable hardness portion.

4. The guide wire according to claim 2, wherein the variable hardness portion has a low hardness part exhibiting a hardness lower than a hardness of the distal end portion of the second shaft.

5. The guide wire according to claim 4, wherein a length of the low hardness part in the axial direction is longer than the diameter of the second shaft.

6. The guide wire according to claim 1, wherein the variable hardness portion includes the distal end of the second shaft.

7. The guide wire according to claim 1, wherein the second shaft includes a hardness increasing part arranged proximally of the variable hardness portion, the hardness increasing part having a hardness that gradually increases from a distal end of the hardness increasing part to a proximal end of the hardness increasing part.

8. The guide wire according to claim 1, wherein the second shaft is formed of a single material.

9. A method for producing the guide wire according to claim 1, the method comprising:

Preparing the first shaft member and the second shaft member, joining the proximal end of the first shaft member and the distal end of the second shaft member to form a joined member including a joint part where the proximal end of the first shaft member and the distal end of the second shaft member are joined, and forming the variable hardness portion by subjecting a portion of the joined member located proximally of the joint part to heat treatment to soften the portion.

* * * * *